United States Patent [19]
Toppo

[11] Patent Number: 5,985,860
[45] Date of Patent: *Nov. 16, 1999

[54] SYSTEM FOR TRANSDERMAL DELIVERY OF PAIN RELIEVING SUBSTANCES

[76] Inventor: Frank Toppo, 8733 Cremonia Dr., Las Vegas, Nev. 89117

[ * ] Notice: This patent is subject to a terminal disclaimer.

[21] Appl. No.: 08/255,100

[22] Filed: Jun. 7, 1994

Related U.S. Application Data

[63] Continuation-in-part of application No. 07/893,011, Jun. 3, 1992, Pat. No. 5,318,960.

[51] Int. Cl.⁶ ..................................................... A61K 31/60
[52] U.S. Cl. ....................... 514/159; 514/165; 514/226.5; 514/249; 514/313; 514/350; 514/356; 514/404; 514/420; 514/423; 514/562; 514/567; 514/569; 514/570; 514/627; 514/648; 514/772; 514/941; 514/975
[58] Field of Search ..................................... 514/159, 165, 514/226.5, 249, 313, 350, 356, 404, 420, 423, 562, 567, 569, 570, 627, 648, 772, 941, 975

[56] References Cited

U.S. PATENT DOCUMENTS 5,318,960  6/1994  Toppo ....................................... 514/159

*Primary Examiner*—Peter O'Sullivan
*Attorney, Agent, or Firm*—Charles H. Thomas

[57] ABSTRACT

Compositions for pain relieving non-steroidal anti-inflammatory drugs and/or medicaments such as ibuprofen, methotrexate, capsaicin, diphenhydramine, aspirin, methylnicotinate and other medicaments largely soluble in oil, alcohol, and/or water, are produced for transdermal delivery. The composition is manufactured by admixing an appropriate amount of oil surfactant with an appropriate amount of pharmaceutically approved co-solubilizer alcohol to establish a non aqueous phase. The oil surfactant may be a polyethoxylated oil such as castor oil. The co-solubilizer solubilizer may be isopropyl alcohol or virtually any other alcohols except for methanol. Thereafter, an appropriate amount of distilled water is slowly added to the homogeneous or non-aqueous phase to further reduce viscosity. The final admixture is a clear, oil-continuous solution having a viscosity no greater than 850 centistokes as measured by the VST Hoppler method at 25 degrees Celsius. The composition produced has the capacity to affect the individual surface skin cells (corneocytes) and allow the passage of medicaments to sub-dermal afflicted areas deep within the skin.

26 Claims, No Drawings

SYSTEM FOR TRANSDERMAL DELIVERY OF PAIN RELIEVING SUBSTANCES

The present application is a continuation-in-part of U.S. application Ser. No. 893,011 filed on Jun. 3, 1992, now U.S. Pat. No. 5,318,960.

BACKGROUND OF THE INVENTION

1. Field of the Invention

The present invention relates to a composition, and method of manufacture thereof, for transdermal delivery of pain relieving substances directly to afflicted areas of the body.

2. Description of the Prior Art

Debilitating diseases such as rheumatoid arthritis and osteoarthritis afflict 37 million people in the United States. The Arthritis Foundation estimates that 10% of the population of the world and 25% of the population of the United States suffer from arthritis to some degree. Fourteen million work days are lost each year in the United States by arthritis victims.

Arthritis is a disease symptomized by painful joints stemming from inflammation in the joint region. Arthritis attacks young, middle-aged and old people alike. Due to the severity of this disease a number of nonsteroidal anti-inflammatory drugs (NSAIDs) have been developed for the treatment of generalized muscle and joint aches, and for the pain of arthritis. aspirin (acetylsalicylic acid), ibuprofen (2(-isobutylphenyl) propionic acid), methotrexate (N-[4-[(2,4 diamino-6-pteridinyl)-methyl]methylamino]benzoyl)-L-glutamic acid), capsaicin (8 methyl-vanillyl-nonenamide) and diphenhydramine (2-(diphenyl-methoxy)-N,N-dimethylethylamine hydrochloride) are only a few of the medicaments that are available in prescription and over the counter formulations for the alleviation of pain.

Unfortunately these medicaments have major side effects caused by the systemic (typically by oral ingestion) administration. For instance, an example of the side effects of ibuprofen when administered in recommended therapeutic doses (e.g. 1000–2400 mg.qd) are esophagitis, nausea, epigastric pain, heartburn, diarrhea, vomiting, abdominal cramps, bloating and flatulence, dizziness, headache, nervousness, dermatologic rash, blurred or diminished vision, edema, fluid retention, elevated blood pressure, palpitations, gastric or duodenal ulcer, hepatitis, jaundice, gastrointestinal hemorrhage, melena, gastritis, abnormal liver function, kidney damage, kidney failure, acute renal failure, and congestive heart failure in patients with marginal cardiac function. The Physicians Desk Reference (PDR) lists these possible side effects and many more when taking ibuprofen, for example, systemically for the relief of pain.

In addition to these side effects when ibuprofen is administered systemically, only a small amount of the ingested drug is delivered to the specific pain area. An example would be if pain and inflammation exists in the front of the knee, and 1000 mg. of ibuprofen is taken orally. Only a small fraction of the ibuprofen actually reaches the pain area. Also, there is a considerable time lapse between injection and the relief of the pain. Clinical studies have shown that following the ingestion of ibuprofen, as much as 79% of the ingested dose is filtered out by the kidneys and is recovered in the urine within 24 hours. This leaves an average of only 21% of the recommended dose of ibuprofen available for systemic distribution throughout the body. Also, the amount of time for relief of pain with systemic application of the drug is between 45 minutes and 120 minutes.

SUMMARY OF THE INVENTION

Transdermal delivery for pain of anti-inflammatory drugs and/or medicaments such as ibuprofen, methotrexate, capsaicin, aspirin, and other NSAIDs, alleviates the side effects caused by the systemic application. The transdermal delivery method will allow the drugs and/or medicaments to be delivered precisely into the body at specific area of pain. Transdermal delivery will relieve pain in 1 to 5 minutes. Also, the amount of medicament needed is much less, being on the order of 50 mg. versus the 1000–2400 mg. needed when ibuprofen is taken orally.

In order for a medicament to have a chance of being delivered transdermally certain suitable physio-chemical properties must be present. That is, the drug must be stable, have a molecular weight less than 1000, a melting point less than about 93 degrees Celsius, a solubility in oil and water greater than 1 mg/ml and a pH of 5 to 9 in a saturated aqueous solution.

The transdermal delivery system must also be able to influence the intercorneocyte ionic bonds which are present in the stratum corneum layer of the epidermis of the skin. When the attracting force between corneocytes is due to ionic bonding, the presence or absence of water can modify force of such bonding considerably. This occurs because the magnitude of attracting force between two opposite electric charges varies directly with the magnitude of the two charges, inversely with the square of the distance between the charges, and inversely with the dielectric constant (inductivity or conductivity of a substance) of the medium substance filling the space between the charges.

When the stratum corneum becomes hydrated, the distance between corneocytes, i.e., between apposing charged groups on outer cell walls of corneocytes, is increased. This results in a decrease in cohesion force. As a quantitative example, if the intercorneocyte distance is doubled the cohesion force between corneocytes is decreased to one fourth. On the other hand, if the stratum corneum is dehydrated and the apposing charged groups on the outer cell walls of corneocytes are decreased to one half, the cohesion force is quadrupled.

The importance of water with a dielectric constant of 1, as compared to air with a value of 1, is illustrated in the hypothetical extreme circumstance in which a completely dehydrated stratum corneum becomes saturated with water. In this circumstance, the intercorneocyte cohesion force is decreased to 1/81 of that present in the dehydrated state.

The present invention is a method of manufacturing a transdermal delivery system for pain relieving drugs and a transdermal pain reliever composition for transdermal delivery. The transdermal delivery composition produced by the method of the invention, when applied to the skin, results in a marked decrease in intercorneocyte cohesion force. The transdermal delivery system thereby allows the pain relieving substances to penetrate through the skin and reach the painful, afflicted area therebeneath.

In one broad aspect the present invention may be considered to be a method of manufacturing a transdermal delivery system which, when applied to the skin of a patient, will deliver pain relieving substances directly to an afflicted area of the body. According to the invention an oil continuous solution is produced containing the pain relieving substance, an oil surfactant, a co-solubilizer and water.

In another broad aspect the present invention may be considered to be a transdermal delivery composition comprising an oil continuous solution of a pain relieving substance, an oil surfactant, a co-solubilizer, and water, which solution has a viscosity no greater than 850 centistokes. Viscosity is measured by the VST Hoppler method at 25 degrees Celsius. Preferably the viscosity is no greater than 700 centistokes.

The quantitative composition of the several components of the composition may vary considerably, depending upon the pain reliever involved and the particular oil surfactant and co-solubilizer employed. However, there are certain maximum quantities of the various components. In the final oil continuous solution there are upper limits for each of the components in the transdermal delivery composition of the invention. Each 100 milliliters of the final oil continuous solution should contain no more than about 15 grams of pain reliever, no more than about 40% oil surfactant by volume, nor more than about 21% co-solubilizer by volume, and no more than about 29% water by volume. The water is preferably distilled water.

Each of the materials, the oil-surfactant, co-solubilizer alcohol and water is important in all of the above formulations. However, in order to achieve a system capable of transdermal delivery, a continuous oil phase must be maintained in all the solutions, while maintaining a sufficiently low viscosity. The term continuous phase, as used herein, means that when combinations of substances are mixed, they give rise to only one phase. In the final product produced according to the invention this single phrase must be a continuous oil phase.

The pain relieving substance may be any one or more of a number of medicaments, including non-steroidal anti-inflammatory drugs which are now administered systemically. These include ibuprofen (2 (isobutylphenyl)propionic acid); methotrexate N-[4-(2,4 diamino 6-pteridinyl-methyl] methylamino]benzoyl)-L-glutamic acid; aspirin (acetylsalicylic acid); salicylic acid; capsaicin (8 methyl-vanillyl-nonenamide); diphenhydramine (2-(diphenyl-methoxy)-N,N-dimethylethylamine hydrochloride; naproxen (2-naphthaleneacetic acid, 6-methoxy-9-methyl-, sodium salt, (-)); phenylbutazone (4-butyl-1,2-diphenyl-3, 5-pyrazolidinedione); sulindac-(2)-5-fuoro-2-methyl-1-[[p-(methylsulfinyl)phenyl]methylene-]-1H-indene-3-acetic acid; diflunisal(2',4',-difluoro-4-hydroxy-3biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl)anthranilic acid, sodium salt, monohydrate); ketoprofen (2-(3-benzoylphenyl)-propionic acid; tolmetim sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1, 1'biphenyl]-4-acetic acid, 2-fluoro-alphamethyl-, (±)); cetodolac (1-8-diethyl-13,4,9, tetra hydropyrano-[3-4-13] indole-1-acetic acid; mefenamic acid (N-(2,3-xylyl)-anthranilic acid; and diphenhydramine hydrochloride (2-diphenyl methoxy-N,N-di-methylethamine hydrochloride).

The oil surfactant is a surface active compound or other material that has the ability to alter that is, reduce, surface tension of materials that are dissolved into it. Suitable oil surfactants include polyethoxylated castor oil, ethoxylated soribitans, sorbitan fatty acid esters, ethoxylated sorbitol and sorbitol esters, ethoxylated fatty acids, polyethylene glycol fatty acids esters, ethoxylated alcohols and ethoxylated triglycerides. Most polyethoxylated vegetable oils can be used as the oil surfactant necessary to the practice of the invention.

The co-solubilizer is a product which has the ability to dissolve in oil, alcohol or a water phase. The co-solubilizer is important because not only are the pain relieving drugs partially or completely dissolvable in oil, water or alcohol, but they also have the ability to dissolve into each of the other solvents when they are in solution.

Virtually any alcohol except methanol may serve as the co-solubilizer. Isopropyl alcohol is one co-solubilizer of choice. Other suitable co-solubilizers include glycerin propylene glycol, polyethylene glycol, and other alcohols such as a SD-3A and cetyl alcohol.

A primary object of the present invention is to provide a method for manufacturing a transdermal delivery system for delivering pain relievers through the skin of a patient directly to the site of affliction. Another object of this invention is the provision of a transdermal delivery system comprising pain and anti-inflammatory drugs and/or medicaments for transdermal application into specific sites of the body. Further, it is an object of this invention to provide a transdermal delivery system comprising ibuprofen, methotrexate, aspirin etc. alone and in combination with capsaicin, diphenhydramine, or methyl-nicotinate.

It is a further object to provide a transdermal delivery system for drugs and/or medicaments largely soluble in oil, drugs and/or medicaments largely soluble in alcohol and also drugs and/or medicaments largely soluble in water.

In the case of largely oil soluble drugs and medicaments such as ibuprofen, transdermal delivery can be achieved by admixing an appropriate amount of an oil surfactant, such as polyethoxylated castor oil, with an appropriate amount of the oil soluble drug. The solubility of such a drug can be accelerated by using heat, agitation and mixing. However, the amount of heat should never exceed 40 degrees Celsius. After the oil soluble drug is in solution with the oil surfactant an appropriate amount of pharmaceutical grade co-solubilizer alcohol is admixed in the oil and pain relieving drug solution to obtain a non aqueous continuous phase.

To the non-aqueous phase an appropriate amount of distilled water is slowly added, with agitation, to reduce viscosity. The resulting mixture is cooled to provide a visibly clear, oil-continuous solution suitable for transdermal delivery at selected areas on the body.

In the case of largely alcohol soluble drugs and/or medicaments such as capsaicin, transdermal delivery can be achieved by first dissolving the capsaicin in an appropriate amount of pharmaceutical grade co-solubilizer such as isopropyl alcohol, and then adding an appropriate amount of an oil surfactant, such as polyethoxylated castor oil, with agitation until a non-aqueous continuous phase is obtained.

An appropriate amount of distilled water is slowly added to the non-aqueous continuous phase, with agitation, to reduce viscosity. The resulting mixture provides a visibly clear, oil-continuous solution suitable for transdermal delivery into a selected area of the body.

In the case of largely water soluble drugs and/or medicaments, such as phenylbutazone, transdermal delivery can be achieved by admixing an appropriate amount of oil surfactant, such as polyethoxylated castor oil, with an appropriate amount of a pharmaceutical grade co-solubilizer alcohol. These substances are admixed to obtain a non-aqueous continuous phase.

After the oil surfactant and co-solubilizer alcohol solution is sufficiently mixed, the water soluble drug or medicaments such as phenylbutazone are dissolved in an appropriate amount of distilled water. The water and water soluble drug solution are slowly added to the non-aqueous continuous phase with agitation and a slight amount of heat; however, the heat is never to exceed 40 Celsius. The resulting mixture is cooled to provide a visibly clear, oil continuous solution that is suitable for transdermal delivery into selected areas of the body.

Some medicaments, for example methotrexate, are not soluble in water, oil or alcohol. They must first be put in solution, using, for example, sodium chloride or a strong acid, prior to the admixing.

Specifically, one ml concentration 25 mg/ml of methotrexate in a sodium chloride solution is added to an 80 ml solution of equal amounts of 99% alcohol and an ethoxylated oil while stirring until a clear yellow aqueous solution appears. Thereafter, QS to 100 ml with either 20 ml of ethoxylated oil and alcohol solution or 20 ml of sodium chloride, depending on the desired viscosity.

In many instances it may be desirable to combine pain relieving drugs and medicaments in a transdermal delivery system according to the invention. For example, it is often desirable to combine specific pain relieving substances with capsaicin in the oil continuous transdermal delivery system produced. Local applications of capsaicin to the peripheral axon of a nerve cell results in a depletion of substance P (SP) from the whole neuron, both peripherally and centrally. SP is a neurotransmitter which means that it is a hormone-like substance that transmits the pain impulse peripherally, such as through the skin, to the central nervous system, namely the brain. Other neurotransmitters, such as calcitonin, gene-related peptide, somatostatin, vasoactive intestinal polypeptide, neurokinin A and neurokinin B, and others, may be similarly effected by capsaicin.

Capsaicin affects C fibers receiving input from polymodal nociceptors which have a conduction velocity of 0.7 m/sec-l, which may represent as much as 80% of all C fiber inputs. Therefore, without SP the transmission of the pain impulse to the brain is severely impaired.

In some instances it may also be highly desirable to combine one or more pain relieving substances with diphenhydramine 2-(Diphenyl-methoxy-N,N-dimethylethylamine hydrochloride which is sold commercially as Benadryl. Benadryl may also be employed to advantage with combinations of capsaicin and other pain relievers.

In every injury to the tissue there is a neurogenic response in the form of a flare reaction on the skin and a wheal response. The flare reaction is mediated by SP and other neurotackykinins and is blocked by capsaicin. A wheal response is a raised edematous area on the skin. The wheal response is a result of vasodilation with subsequent protein extravasation. The wheal is caused by histamine being released from mast cells. The use of Benadryl blocks this wheal response, thus alleviating this skin reaction.

In some instances it may also be highly desirable to combine one or more pain relieving substances with methyl-nicotinate (3-Pyridinecarboxylic acid methyl ester) which is obtained by passing hydrogen chloride gas into a hot methanol solution of nicotinic acid. Nicotinic acid is a B-vitamin (niacin) which is found in liver, beef, pork, whole grain cereals, yeast, fruits and most vegetables. Niacin is also manufactured by the bacteria present in human intestines.

Methyl-nicotinate is a counter irritant that produces vasodilation without extravasation of protein and serum from the intravascular compartment. This vasodilation may facilitate the absorption of various medicaments. Methyl-nicotinate is soluble in both water and alcohol.

The three non-aqueous liquids have infinite mutual solubilities. The dissolution of the drugs and/or medicaments can retard this mutual solubility and limit the solubilization of water. It is impractical to detail the exact optimum formulation of all drugs and medicaments that can be administered through the method of transdermal delivery according to the invention. However the preferred practice of the invention may be described with reference to several specific examples.

EXAMPLE ONE

Forty milliliters of polyethoxylated oil are measured into a suitable container. Ten grams of ibuprofen are added to the container while stirring and heating. The temperature should not be allowed to exceed forty degrees Celsius. Twenty one milliliters of a pharmaceutical grade alcohol, such as isopropyl alcohol, are then added to the ethoxylated oil and ibuprofen.

Once the foregoing mixture of materials is in a clear solution, distilled water QS is then added to create a total volume of one hundred milliliters. If an odiferous counter irritant such as menthol is desired, it should be added prior to the addition of the distilled water to the final solution. The final solution is cooled to ambient temperature. This resultant product will be a visibly clear, oil continuous transdermal solution containing ibuprofen to the extent of ten percent by weight.

EXAMPLE TWO

Example One is repeated with the exception that an equal weight of naproxen is substituted for the ibuprofen of Example One.

EXAMPLE THREE

Example One is repeated with the exception that an equal weight of cetodolac is substituted for the ibuprofen of Example One.

EXAMPLE FOUR

Example One is repeated with the exception that an equal weight of sulindac is substituted for the ibuprofen of Example One.

EXAMPLE FIVE

Ibuprofen and capsaicin are combined in a transdermal delivery system formed as an oil continuous solution. Forty mls. of polyethoxylated oil is measured into a suitable container. Ten grams of ibuprofen are added to the container while stirring and heating the contents of the container. The temperature is not allowed to exceed 40 degrees Celsius.

Twenty one mls. of pharmaceutical grade alcohol, such as isopropyl alcohol, and nine mls. of distilled water are measured into a second suitable container while stirring and heating that mixture. Seventy-five mgs. of 100% pure capsaicin along with an odiferous counterirritant, such as one gram of crystals of menthol, are measured separately and added to the second container. Stirring and heating of the contents of the second container is continued until the capsaicin and menthols are dissolved.

Next forty mls. of the mixture of ethoxylated oil and ibuprofen is slowly added to the second container. Once the above materials are in a clear solution, distilled water QS is slowly added to the second container to produce a total volume of 100 mls. The resultant mixture is cooled to ambient temperature. The end product is a visibly clear, oil-continuous transdermal solution containing 10% by weight of ibuprofen, 1% menthol, and 0.075% by weight of capsaicin.

EXAMPLE SIX

Twenty milliliters of distilled water are poured into a suitable container while stirring and heating. Ten grams of phenylbutazone are added to the heated water. Twenty one milliliters of pharmaceutical grade alcohol, such as isopropyl alcohol, are added. The temperature of this mixture should not exceed forty degrees Celsius.

Forty milliliters of polyethoxylated oil are next slowly added to the container, while stirring and heating is continued. Once all of the foregoing materials are in a clear solution, distilled water QS is added to create a total volume of 100 milliliters. This volume is cooled to ambient temperature. The end product will be a visibly clear oil continuous, transdermal solution containing ten percent by weight of phenylbutazone.

EXAMPLE SEVEN

Example Five is repeated with the substitution of an equal weight of piroxicam for the phenylbutazone of Example Five.

EXAMPLE EIGHT

Example Five is repeated with the substitution of an equal weight of diflunisal for the phenylbutazone of Example Five.

EXAMPLE NINE

Example Five is repeated with the substitution of an equal weight of hyroxychloroquine sulfate for the phenylbutazone of Example Five.

EXAMPLE TEN

Example Five is repeated with the substitution of an equal weight of penicillamine for the phenylbutazone of Example Five.

EXAMPLE ELEVEN

Example Five is repeated with the substitution of an equal weight of meclofenamic acid and sodium salt for the phenylbutazone of Example Five.

EXAMPLE TWELVE

Example Five is repeated with the substitution of an equal weight of tamarind for the phenylbutazone of Example Five.

EXAMPLE THIRTEEN

Example Five is repeated with the substitution of an equal weight of mefenamic acid for the phenylbutazone of Example Five.

EXAMPLE FOURTEEN

Example Five is repeated with the substitution of an equal weight of diclofenac sodium for the phenylbutazone of Example Five.

EXAMPLE FIFTEEN

Example Five is repeated with the substitution of an equal weight of diphenhydramine hydrochloride for the phenylbutazone of Example Five.

EXAMPLE SIXTEEN

Twenty one milliliters of isopropyl alcohol, or some other pharmaceutical grade alcohol, is measured into a suitable container while stirring and heating. To this mixture ten grams of salicylic acid are added. The temperature should not be allowed to exceed forty degrees Celsius. To this mixture forty milliliters of polyethoxylated oil are added, while continuously stirring and heating. Once the foregoing material are in a clear solution, distilled water QS is slowly added to a total volume of 100 milliliters. The mixture is cooled to ambient temperature. The end product will be a visibly clear, oil continuous, transdermal solution containing salicylic acid to the extent of ten percent by weight.

EXAMPLE SEVENTEEN

The formulation of Example Seventeen is repeated with the substitution of an equal weight of aspirin for salicylic acid.

EXAMPLE EIGHTEEN

The formulation of Example Seventeen is repeated with the substitution of an equal weight of indomethacin for salicylic acid.

EXAMPLE NINETEEN

The formulation of Example Seventeen is repeated with the substitution of an equal weight of ketoprofen for salicylic acid.

EXAMPLE TWENTY

Salicylic acid and capsaicin are combined in a transdermal delivery system formed as an oil continuous solution. Twenty one mls of pharmaceutical grade alcohol, such as isopropyl alcohol, and nine mls of distilled water are measured and added to a suitable container while stirring and heating. A quantity of six grams of salicylic acid is then added to the mixture. The temperature is not allowed to exceed forty degrees Celsius.

Seventy-five mgs. of 100% pure capsaicin are separately measured along with an odiferous counterirritant such as one gram of crystals of menthol. The capsaicin and menthol are added to the alcohol/salicylic acid mixture. Stirring and heating is continued until the capsaicin and menthol are dissolved. Next, distilled water QS is slowly added to produce a total volume of 100 mls. The mixture is then cooled to ambient temperature. The end product is a visibly clear, oil-continuous transdermal solution containing 6% by weight of salicylic acid, 1% menthol and 0.075% by weight of capsaicin.

EXAMPLE TWENTY-ONE

The formulation of Example Five is repeated with the substitution of an equal weight of diphenhydramine for the capsaicin of Example Five.

EXAMPLE TWENTY-TWO

Example Five is repeated with the substitution of an equal weight of methyl-nicotinate for the capsaicin of Example Five.

EXAMPLE TWENTY-THREE

The formulation of Example Seven is repeated with the substitution of an equal weight of diphenhydramine for the capsaicin of Example Seven.

EXAMPLE TWENTY-FOUR

Example Seven is repeated with the substitution of an equal weight of methyl-nicotinate for the capsaicin of Example Seven.

EXAMPLE TWENTY-FIVE

The formulation of Example Eight is repeated with the substitution of an equal weight of diphenhydramine for the capsaicin of Example Eight.

EXAMPLE TWENTY-SIX

Example Eight is repeated with the substitution of an equal weight of methyl-nicotinate for the capsaicin of Example Eight.

EXAMPLE TWENTY-SEVEN

The formulation of Example Nine is repeated with the substitution of an equal weight of diphenhydramine for the capsaicin of Example Nine.

EXAMPLE TWENTY-EIGHT

Example Nine is repeated with the substitution of an equal weight of methyl-nicotinate for the capsaicin of Example Nine.

EXAMPLE TWENTY-NINE

The formulation of Example Ten is repeated with the substitution of an equal weight of diphenhydramine for the capsaicin of Example Ten.

EXAMPLE THIRTY

Example Ten is repeated with the substitution of an equal weight of methyl-nicotinate for the capsaicin of Example Ten.

EXAMPLE THIRTY-ONE

The formulation of Example Eleven is repeated with the substitution of an equal weight of diphenhydramine for the capsaicin of Example Eleven.

EXAMPLE THIRTY-TWO

Example Eleven is repeated with the substitution of an equal weight of methyl-nicotinate for the capsaicin of Example Eleven.

EXAMPLE THIRTY-THREE

The formulation of Example Twelve is repeated with the substitution of an equal weight of diphenhydramine for the capsaicin of Example Twelve.

EXAMPLE THIRTY-FOUR

Example Twelve is repeated with the substitution of an equal weight of methyl-nicotinate for the capsaicin of Example Twelve.

EXAMPLE THIRTY-FIVE

The formulation of Example Thirteen is repeated with the substitution of an equal weight of diphenhydramine for the capsaicin of Example Thirteen.

EXAMPLE THIRTY-SIX

Example Thirteen is repeated with the substitution of an equal weight of methyl-nicotinate for the capsaicin of Example Thirteen.

EXAMPLE THIRTY-SEVEN

The formulation of Example Fourteen is repeated with the substitution of an equal weight of diphenhydramine for the capsaicin of Example Fourteen.

EXAMPLE THIRTY-EIGHT

Example Fourteen is repeated with the substitution of an equal weight of methyl-nicotinate for the capsaicin of Example Fourteen.

EXAMPLE THIRTY-NINE

The formulation of Example Fifteen is repeated with the substitution of an equal weight of diphenhydramine for the capsaicin of Example Fifteen.

EXAMPLE FORTY

Example Fifteen is repeated with the substitution of an equal weight of methyl-nicotinate for the capsaicin of Example Fifteen.

EXAMPLE FORTY-ONE

The formulation of Example Twenty is repeated with the substitution of an equal weight of diphenhydramine for the capsaicin of Example Twenty.

EXAMPLE FORTY-TWO

Example Twenty is repeated with the substitution of an equal weight of methyl-nicotinate for the capsaicin of Example Twenty.

EXAMPLE FORTY-THREE

The formulation of Example Twenty is repeated with the substitution of an equal weight of diphenhydramine for the capsaicin and an equal weight of ketoprofen for the salicylic acid of Example Nineteen.

EXAMPLE FORTY-FOUR

The formulation of Example Twenty is repeated with the substitution of an equal weight of methyl-nicotinate for the capsaicin and an equal weight of ketoprofen for the salicylic acid of Example Twenty.

EXAMPLE FORTY-FIVE

The formulation of Example Twenty is repeated with the substitution of an equal weight of methyl-nicotinate for the capsaicin and an equal weight of indomethacin for the salicylic acid of Example Twenty.

EXAMPLE FORTY-SIX

The formulation of Example Twenty is repeated with the substitution of an equal weight of methyl-nicotinate for the capsaicin and an equal weight of indomethacin for the salicylic acid of Example Nineteen.

EXAMPLE FORTY-SEVEN

The formulation of Example Twenty is repeated with the substitution of an equal weight of diphenhydramine for the capsaicin and an equal weight of aspirin for the salicylic acid of Example Nineteen.

EXAMPLE FORTY-NINE

The formulation of Example Twenty is repeated with the substitution of an equal weight of methyl-nicotinate for the capsaicin and an equal weight of aspirin for the salicylic acid of Example Twenty.

Undoubtedly, numerous variations and modifications of the invention will become readily apparent to those familiar with transdermal drug and medication delivery systems. Accordingly, the scope of the invention should not be construed as limited to the specific examples depicted and described, but rather is defined in the claims appended hereto.

I claim:

1. A transdermal delivery composition comprising an oil continuous solution of a pain relieving substance, an oil surfactant, a co-solubilizer, and water and having a viscosity of no greater than 850 centistokes, and wherein said pain relieving substance is selected from the group consisting of ibuprofen, methotrexate, aspirin, salicylic acid, capsaicin, diphenhydramine, naproxen, phenylbutazone, sulindac, diflunisal, piroxicam, indomethacin, meclofenamate sodium, ketoprofen, tolmetin sodium, diclofenac sodium, hydroxychloroquine sulphate, penicillamine, flurbiprofen, mefenamic acid, diphenhydramine hydrochloride, cetodolac, and methyl-nicotinate, and wherein said pain relieving substance comprises no more than about 15 grams of each 100 milliliter volume of said oil continuous solution, said oil surfactant comprises no more than about 40% of said oil continuous solution by volume, said co-solubilizer comprises no more than about 21% of said oil continuous solution by volume, and said water comprises no more than about 29% of said oil continuous solution by volume.

2. A transdermal delivery composition according to claim 1 wherein said water is distilled water.

3. A transdermal delivery composition according to claim 2 wherein said distilled water comprises no more than 29% of said oil continuous solution by volume.

4. A transdermal delivery composition according to claim 1 wherein said pain reliever is comprised of ibuprofen.

5. A transdermal delivery composition according to claim 1 wherein said pain reliever is comprised of methotrexate.

6. A transdermal delivery composition according to claim 1 wherein said pain reliever is comprised of capsaicin.

7. A transdermal delivery composition according to claim 1 wherein said pain reliever is comprised of diphenhydramine.

8. A transdermal delivery composition according to claim 1 wherein said pain reliever is comprised of methyl-nicotinate.

9. A transdermal delivery system according to claim 1 wherein said pain reliever is comprised of at least one substance selected from the group consisting of capsaicin, aspirin, salicylic acid, methyl-nicotinate, indomethacin and ketoprofen.

10. A transdermal deliver system according to claim 9 further comprising capsaicin and at least one substance selected from the group consisting of aspirin, salicylic acid, indomethacin and ketoprofen.

11. A transdermal delivery system according to claim 10 further comprising diphenhydramine.

12. A transdermal delivery composition according to claim 9 wherein said co-solubilizer is comprised of an alcohol.

13. A transdermal delivery composition according to claim 9 wherein said co-solubilizer is comprised of isopropyl alcohol.

14. A transdermal delivery composition according to claim 9 wherein said co-solubilizer is selected from the group consisting of isopropyl alcohol, glycerin, propylene glycol, polyethylene glycol, SD-3A and ethyl alcohol.

15. A transdermal delivery composition according to claim 9 wherein said oil surfactant is comprised of polyethoxylated castor oil.

16. A transdermal delivery composition according to claim 9 wherein said oil surfactant is comprised of an ethoxylated sorbitan.

17. A transdermal delivery composition according to claim 9 wherein said oil surfactant is comprised of a sorbitan fatty acid ester.

18. A transdermal delivery composition according to claim 9 wherein said oil surfactant is an comprised of an ethoxylated sorbitol.

19. A transdermal delivery composition according to claim 9 wherein said oil surfactant is comprised of a sorbitol ester.

20. A transdermal delivery composition according to claim 9 wherein said oil surfactant is an comprised of an ethoxylated fatty acid.

21. A transdermal delivery composition according to claim 9 wherein said oil surfactant is comprised of a polyethylene glycol fatty acid ester.

22. A transdermal delivery composition according to claim 9 wherein said oil surfactant is comprised of an ethoxylated alcohol.

23. A transdermal delivery composition according to claim 9 wherein said oil surfactant is an comprised of an ethoxylated triglyceride.

24. A transdermal delivery composition according to claim 9 wherein said oil surfactant is comprised of a polyethoxylated vegetable oil.

25. A transdermal delivery composition according to claim 1 wherein said pain reliever is comprised of at least one substance selected from the group consisting of phenylbutazone, diflunisal, peroxicam, hydroxychloriquine sulfate, penicillamine, meclofenamic acid and sodium salt, tolmetin and sodium salt, mefenamic acid, diclofenac sodium, diphenhydramine and methyl-nicotinate.

26. A transdermal delivery composition according to claim 1 wherein said pain reliever is comprised of at least one substance selected from the group consisting of ibuprofen, naproxen, cetodolac, flurbiprofen and sulindac.

* * * * *